(12) United States Patent
Schweinsberg et al.

(10) Patent No.: US 8,609,078 B2
(45) Date of Patent: *Dec. 17, 2013

(54) COMPOSITION FOR SHAPING KERATIN FIBERS CONTAINING STARCHES MODIFIED WITH PROPYLENE OXIDE

(75) Inventors: Matthias Schweinsberg, Hamburg (DE); Ralf Roenisch, Wuppertal (DE); Mathias Schriefers, Moenchengladbach (DE); Carine Dogan, Vigneux sur Seine (FR)

(73) Assignee: Henkel AG & Co. KGaA, Düsseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,585

(22) Filed: Apr. 23, 2012

(65) Prior Publication Data

US 2012/0207695 A1     Aug. 16, 2012

Related U.S. Application Data

(63) Continuation of application No. PCT/EP2010/065864, filed on Oct. 21, 2010.

(30) Foreign Application Priority Data

Oct. 22, 2009   (DE) .......................... 10 2009 045 925

(51) Int. Cl.
    *A61K 8/73*          (2006.01)
(52) U.S. Cl.
    USPC ..................................... 424/70.13
(58) Field of Classification Search
    None
    See application file for complete search history.

(56) References Cited

U.S. PATENT DOCUMENTS

| 4,528,283 A | 7/1985 | Lang et al. |
| 4,780,310 A | 10/1988 | Lang et al. |
| 4,976,952 A | 12/1990 | Lang et al. |
| 5,520,200 A | 5/1996 | Sturla |
| 6,235,913 B1 | 5/2001 | Raths et al. |
| 6,413,505 B1 * | 7/2002 | Vitale et al. ................ 424/70.11 |
| 7,332,466 B2 | 2/2008 | Schmid et al. |

FOREIGN PATENT DOCUMENTS

| AU | 730455 B2 | 5/2000 |
| DE | 19756454 C1 | 6/1999 |
| DE | 10352470 A1 | 6/2005 |
| EP | 0274086 A2 | 7/1988 |
| EP | 0580514 A1 | 1/1994 |
| EP | 0948958 A2 | 10/1999 |
| EP | 0948959 A2 | 10/1999 |
| EP | 0948960 A2 | 10/1999 |
| EP | 1317916 A2 | 6/2003 |
| WO | 02083089 A1 | 10/2002 |

OTHER PUBLICATIONS

International Cosmetic Ingredient Dictionary & Handbook. The Cosmetic Toiletry and Fragrance Association, 7th Edition, 1997.
Gottschalck, T.E. et al. "International Cosmetic Ingredient Dictionary and Handbook." The Cosmetic, Toiletry and Fragrance Association, 12th Edition, vol. 3, 2008, pp. 3187-3192 and 3214-3215, XP002627782.

* cited by examiner

*Primary Examiner* — Anand Desai
*Assistant Examiner* — Melissa Mercier
(74) *Attorney, Agent, or Firm* — Ingrassia Fisher & Lorenz, P.C.

(57) ABSTRACT

Cosmetic agents for temporary deformation of keratinic fibers containing, in a cosmetic carrier, at least one starch modified with propylene oxide and having an average molecular weight (weight average) of from 50 to 2500 kDa, the agents enabling a hairstyle with strong hold and high flexibility. Starches modified with propylene oxide are based on renewable raw materials. In this way, effective styling products for hair are provided without having to use raw materials based on fossil fuels.

15 Claims, No Drawings

COMPOSITION FOR SHAPING KERATIN FIBERS CONTAINING STARCHES MODIFIED WITH PROPYLENE OXIDE

CROSS REFERENCE TO RELATED APPLICATIONS

The present application is a continuation of International Application No. PCT/EP2010/065864 filed 21 Oct. 2010, which claims priority to German Patent Application No. 10 2009 045 925.1 filed 22 Oct. 2009, both of which are incorporated herein by reference.

The present invention relates to cosmetic agents for the temporary deformation of keratinic fibers containing, in a cosmetic carrier, at least one starch modified with propylene oxide that have an average molecular weight (weight average) from 50 to 2500 kDa.

Styling agents for the deformation of keratinic fibers have been known for some time and are used in various embodiments to build up, refresh, and fix in place hairstyles that, for many types of hair, can be obtained only with the use of setting active substances. An important role is played in this context both by hair treatment agents that serve for permanent shaping, and those serving for temporary shaping of the hair. Temporary shaping operations that are intended to yield good hold without impairing the healthy appearance of the hair such as its shine, can be achieved, for example, using hair sprays, hair waxes, hair gels, blow-dry waves, etc.

Corresponding agents for temporary shaping usually contain synthetic polymers as a shaping component. Preparations containing a dissolved or dispersed polymer can be applied onto hair using propellant gases or a pump mechanism. Hair gels and hair waxes, however, are not applied directly onto the hair but instead distributed in the hair using a comb or one's hands.

Synthetic polymers usually used in agents for temporary shaping are manufactured from corresponding synthetically accessible monomers. These monomers are obtained from fossil substances such as petroleum by conversion to the corresponding polymer modules, in some cases with expenditure of energy.

In a more sustainable approach to nature as living space, and to resources, it is still desirable to use in cosmetic products only those cosmetic raw materials that are accessible, with as little energy use as possible, from renewable raw materials. A reduction in the amount or even a replacement of the aforesaid synthetic polymers can be undertaken, however, only when the substitute exhibits those properties desired for the intended application and ensures a sufficiently stable hold and shape for the keratin-containing fibers.

In addition, nature-based substitute polymers should retain the elasticity and smoothness of the keratin-containing fibers that are fixed as to shape. Formation on keratin-containing fibers of polymer particles visible to the naked eye must be avoided. In addition, the keratin-containing fibers must not give a dull impression but instead should have a natural shine.

The present invention therefore provides a cosmetic composition, acting in shape-fixing fashion based predominantly or completely on renewable raw materials, that produces improved shape fixing and that does not have the aforementioned disadvantages. The intention is to be able to dispense as completely as possible with the use of synthetic polymers based on fossil raw materials.

A first subject of the invention is therefore a cosmetic agent for temporary deformation of keratinic fibers, particularly human hair, containing, in a cosmetic carrier, at least one starch modified with propylene oxide, having an average molecular weight (weight average) from 50 to 2500 kDa. These agents have outstanding parameters for use on hair. The aforesaid starch can be incorporated into the agents according to the present invention simply by mixing almost without the use of heat, at a maximum of 30° C.

"Keratinic fibers" according to the present invention includes furs, wool, feathers, and particularly human hair.

Starch is a reserve carbohydrate that is stored by many plants in the form of large starch grains (granules), usually 1 to 200 μm in size, in various parts of the plant, for example, in tubers or roots, cereal seeds, fruits and in the pith. A starch modified with propylene oxide that can be used according to the invention can be obtained from the starch of potatoes, corn, rice, peas, acorns, chestnuts, barley, wheat, bananas, sago, millet, sorghum, oats, barley, rye, beans, yams, arrowroot or cassava. Particularly pronounced effects according to the present invention are achieved with tapioca starch modified with propylene oxide, with a potato starch modified with propylene oxide, and with mixtures of the two aforesaid starches. Very preferably, the agent according to the present invention contains at least one potato starch modified with propylene oxide.

Starch belongs to the homoglycan family and is a polycondensation product of D-glucose. Starch is made up of three structurally different polymers of d-glucopyranose, namely amylose, amylopectin, and an intermediate fraction. Higher plants contain 0 to 45 wt % amylose, based on the dry substance.

The intermediate fraction, also referred to as "anomalous amylopectin," is structurally intermediate between amylose and amylopectin. The quantitative indications defined in the context of this Application for amylopectin include the intermediate fraction.

Preferably, the starch modified with propylene oxide has an amylose content of less than 25 wt %, particularly less than 20 wt %, based on the weight of the starch. Starch having 17 to 22 wt % amylose and 78 to 83 wt % amylopectin is particularly suitable for achieving the effect according to the present invention.

Amylose is made up of predominantly linear α-1,4-glycosidically linked d-glucose, $M_r$ 50,000 to 150,000. The resulting chains form double helices in the starch.

In addition to the α-1,4 links described for amylose, amylopectin also contains α-1,6 bonds (in an amount of 4 to 6%) as branching points. The average spacing between the branching points is equal to approximately 12 to 17 glucose units. The molar mass of $10^7$ to $7*10^8$ corresponds to approximately $10^5$ glucose units, making amylopectin one of the largest biopolymers. The branching points are distributed over the molecule so that a bundle structure with relatively short side chains develops. Each double helix is formed by two of these side chains. As a result of the many branching points, amylopectin is relatively easily soluble in water.

"Starch modified with propylene oxide" according to the present invention refers to a reaction product of a starch with propylene oxide. A reaction product of this kind includes at least one structural unit of formula (PS)

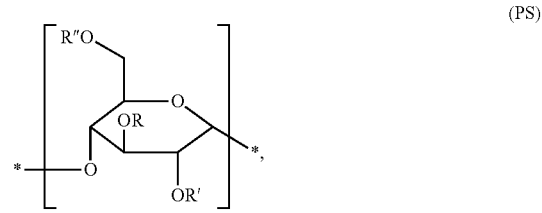

wherein at least one of R, R', or R" is a group of the formula

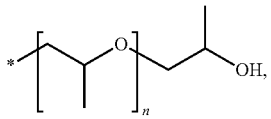

wherein n is greater than or equal to zero, and at most two of the residues from among R, R', and R" is a hydrogen atom. In formulae of this Application, a bond labeled with the symbol "*" corresponds to a free valence of the corresponding structural unit. Starches modified with propylene oxide are provided, for example, by reacting a natural starch with propylene oxide. Before modification with propylene oxide, the starch can have been exposed to a variety of physical or chemical processes, for example, heat treatment, shear, thermal, acid-hydrolytic, oxidizing, enzymatic cleavage, etc.

It is preferred according to the present invention if the starch modified with propylene oxide is not present in the agent in the form of individual starch grains (granules). For this purpose, starch grains are disintegrated, for example, by heat or shear and the corresponding polysaccharide molecules are released from the composite material. The released polysaccharide molecules are modified with propylene oxide after or before release.

In a preferred embodiment, the starch modified with propylene oxide is gelatinized. When an aqueous suspension of starch is heated or compressed, a tangential swelling of the bodies is then observed at a critical temperature or pressure, with loss of birefringence, a change in X-ray structure, and an abrupt rise in the viscosity of the solution. This phenomenon is called "gelatinization".

Starches modified with propylene oxide are present in the agent in a molecular weight distribution. The molecular weight distribution has been determined experimentally by gel filtration chromatography against dextran. An important feature of the invention is the weight average of the average molecular weight of the propylene oxide-modified starches present in the agent according to the present invention. The weight average is an average molecular weight that takes into account total weight of the molecules of various molecular weights, and not simply the number of molecules.

For statistical calculation of the weight average, the "weight break" is first defined:

$$w_i = (N_i M_i)/[\Sigma(N_i M_i)].$$

This indicates the weight proportion in the sample of macromolecules made up of i segments (e.g., monomer modules) of mass $M_i$ and that occur $N_i$ times in the sample. The weight average of the molecular weight $M_w = \Sigma w_i M_i$ is thus given by $$M_w = [\Sigma(N_i M_i^2)]/[\Sigma(N_i M_i)].$$

Preferred agents according to the present invention contain starches modified with propylene oxide having an average molecular weight (weight average) from 100 to 400 kDa, preferably from 200 to 300 kDa. Agents of this embodiment are incorporated preferably into foams or gels as a cosmetic carrier, and are therefore present as a foam or gel. Despite a molecular weight that is low for setting polymers, outstanding setting can be achieved with these starches. In addition, gels manufactured with the starches furthermore achieve superb transparency.

Starches modified with propylene oxide (particularly potato starches modified with propylene oxide) are furthermore particularly preferred for use in agents according to the present invention when they have a molecular weight (weight average) from 100 to 1000 kDa, in particular from 700 to 900 kDa. The agents of this embodiment are incorporated preferably into foams or gels as a cosmetic carrier, and are therefore present as a foam or gel. Despite a molecular weight that is low for setting polymers, outstanding setting can be achieved with these starches. In addition, gels manufactured with the starches furthermore achieve superb transparency.

In order to adjust the molecular weight, the starch is subjected to a mechanical and/or chemical treatment before or after modification with propylene oxide. To elevate the molecular weight, the starch can be crosslinked. Crosslinking of starch modified with propylene oxide exists when the linear or branched polysaccharide macromolecules of the starch are linked covalently by a crosslinking agent, forming a three-dimensional, insoluble, and still swellable polymeric network. Natural starch is generally considered uncrosslinked and, if crosslinking were desirable, requires artificial crosslinking by means of synthesis chemistry. Artificial crosslinking of this kind can be carried out using crosslinking agents. Starches (modified with propylene oxide) that do not exhibit such crosslinking are uncrosslinked.

Crosslinking occurs, for example, by use of the crosslinking agent epichlorohydrin. For this, a 42-wt % mixture of starch modified with propylene oxide in water is produced, into which mixture the desired quantity of epichlorohydrin is stirred at room temperature. Once the target viscosity is reached after a stirring time of 1 to 5 hours with viscosity monitoring, the crosslinked starch is isolated using ordinary methods.

It is preferred, however, if the starch(es) modified with propylene oxide present in agents according to the present invention are uncrosslinked.

To achieve a lower molecular weight from 100 to 400 kDa or 200 to 300 kDa, the starches are preferably exposed to a mechanical cleavage, enzymatic cleavage (particularly using alpha-amylase, beta-amylase, glucoamylase, or debranching enzymes), acid-hydrolytic cleavage (particularly using hydrochloric acid, sulfuric acid, or phosphoric acid), thermal cleavage, or a reaction with oxidizing agents (such as periodate, hypochlorite, chromic acid, permanganate, nitrogen dioxide, hydrogen peroxide, or organic percarboxylic acid, preferably with hydrogen peroxide). Kneaders, extruders, stator/rotor mechanisms, and/or agitators are suitable for mechanical cleavage of the starch.

Oxidative cleavage using hydrogen peroxide is preferred according to the present invention. To accomplish this, for example, starch modified with propylene oxide is added to water, heated to 50 to 70° C., hydrogen peroxide is added, and stirring occurs at 70 to 85° C. for 2 to 5 hours.

Propylene oxide content of the starch affects the fine-tuning of the hairstyle hold and hairstyle flexibility, as well as stability of the cosmetic agents. The parameters can be further optimized if the starch modified with propylene oxide has, based on weight of the starch, propylene oxide content from 1 to 20 wt %, more preferably propylene oxide content from 8 to 12 wt %, very preferably propylene oxide content from 9.5 to 10.5 wt %. In a further embodiment, it may be preferred if the starch modified with propylene oxide has, based on weight of the starch, a propylene oxide content from 1 to 20 wt %, particularly preferably a propylene oxide content from 3 to 10 wt %, very particularly preferably a propylene oxide content from 4.0 to 6.0 wt %. Propylene oxide content can be determined, for example, by carrying out a Hodges cleavage using the method according to DIN EN 13268.

Those cosmetic agents wherein the starch modified with propylene oxide has, in a 43-wt % aqueous solution, a preferred viscosity in the range from 150 to 1,500,000 mPa·s (Brookfield viscosimeter, spindle 7 at 20° C. and 20 rpm) are outstandingly suitable for purposes of the invention. Outstanding suitable propylene oxide-modified polysaccharides have viscosities from 3000 to 80,000 mPa·s, particularly from 10,000 to 100,000 mPa·s, particularly preferably from 40,000 to 70,000 mPa·s, in a specific embodiment particularly preferably from 5000 to 8000 mPa·s (measured under the conditions recited above).

It is preferred if the cosmetic agent contains the polysaccharide modified with propylene oxide in an amount of from 1.0 wt % to 30 wt %, particularly 2.5 wt % to 20 wt %, based on weight of the agent.

The cosmetic agent according to the present invention is preferably free of synthetic film-forming polymers and synthetic setting polymers that have been manufactured using fossil raw materials. "Fossil raw materials" are according to the present invention those substances whose origin derives from fossil fuels.

"Polymers" according to the present invention refer to compounds constructed from a plurality of molecules in which one type or several types of atoms or atom groupings ("constituent units," "basic modules," or "repeating units") are repeatedly serially arranged, and that have a molecular weight of at least 10,000 g/mol. The polymers are obtained by polyreaction, which can occur artificially (i.e., synthetically) or naturally.

"Film-forming polymers" refer to those polymers that, upon drying, leave behind a continuous film on the skin, hair, or nails. Film-formers of this kind can be used in a very wide variety of cosmetic products such as face masks, make-up, hair setting agents, hair sprays, hair gels, hair waxes, hair therapies, shampoos, or nail polishes. Polymers having sufficient solubility in water, alcohol or in water/alcohol mixtures are particularly preferred. It is possible in this way to produce corresponding solutions that can easily be utilized or further processed.

"Film-forming polymers" also refer to those polymers that, when applied in a 0.01- to 20-wt % aqueous, alcoholic, or aqueous alcoholic solution, are capable of depositing a transparent polymer film on the hair. Film-forming polymers can be charged in anionic, amphoteric, nonionic, permanently cationic, or temporarily cationic fashion.

Cosmetic agents having at least one additional polymer are thus preferred with the provision that all additional polymers are polysaccharide-based polymers. These additional polymers differ from the propylene oxide-modified polysaccharides. In further preferred fashion, all further polymers of the cosmetic agent according to the present invention are chosen from xanthan, dehydroxanthan, alginate, guar gum, gum arabic, locust bean gum, starch, chitosan, or mixtures.

The additional polymers are present preferably in an amount from 0.5 wt % to 30 wt %, particularly 2.5 wt % to 20 wt %, based on weight of the agent.

Very particularly preferred cosmetic agents according to the present invention conform to at least one of the following embodiments A) to W):

A): A cosmetic agent for temporary deformation of keratinic fibers, particularly human hair, containing, in a cosmetic carrier, at least one starch modified with propylene oxide and having an average molecular weight (weight average) from 50 to 2500 kDa, preferably from 100 to 400 kDa, more preferably from 200 to 300 kDa, which starch has a propylene oxide content, based on the weight of the starch, from 5 to 15 wt %.

B): A cosmetic agent for temporary deformation of keratinic fibers, particularly human hair, containing, in a cosmetic carrier, at least one starch modified with propylene oxide and having an average molecular weight (weight average) from 50 to 2500 kDa, preferably from 100 to 400 kDa, more preferably from 200 to 300 kDa, which starch has a propylene oxide content, based on the weight of the starch, from 8.0 to 12.0 wt %.

C): A cosmetic agent for temporary deformation of keratinic fibers, particularly human hair, containing, in a cosmetic carrier, at least one starch modified with propylene oxide and having an average molecular weight (weight average) from 50 to 2500 kDa, preferably from 100 to 400 kDa, more preferably from 200 to 300 kDa, which starch has a propylene oxide content, based on the weight of the starch, from 9.5 to 10.5 wt %.

D): A cosmetic agent for temporary deformation of keratinic fibers, particularly human hair, containing, in a cosmetic carrier,
(a) at least one starch modified with propylene oxide and having an average molecular weight (weight average) from 100 to 400 kDa, very particularly preferably from 200 to 300 kDa, which starch has a propylene oxide content, based on weight of the starch, from 5 to 15 wt %, and
(b) at least one additional polymer, with the proviso that all additional polymers are polysaccharide-based polymers.

E): A cosmetic agent for temporary deformation of keratinic fibers, particularly human hair, containing, in a cosmetic carrier,
(a) at least one starch modified with propylene oxide and having an average molecular weight (weight average) from 100 to 400 kDa, more preferably from 200 to 300 kDa, which starch has a propylene oxide content, based on weight of the starch, from 8 to 12 wt %, and
(b) at least one additional polymer, with the proviso that all additional polymers are polysaccharide-based polymers.

F): A cosmetic agent for temporary deformation of keratinic fibers, particularly human hair, containing, in a cosmetic carrier,
(a) at least one starch modified with propylene oxide and having an average molecular weight (weight average) from 100 to 400 kDa, more preferably from 200 to 300 kDa, which starch has a propylene oxide content, based on weight of the starch, from 9.5 to 10.5 wt %, and
(b) at least one additional polymer, with the proviso that all additional polymers are polysaccharide-based polymers.

G): A cosmetic agent for temporary deformation of keratinic fibers, particularly human hair, containing, in a cosmetic carrier, at least one starch modified with propylene oxide that has been degraded with hydrogen peroxide and has an average molecular weight (weight average) from 100 to 400 kDa, more preferably from 200 to 300 kDa, as well as a propylene oxide content, based on the weight of the starch, from 5 to 15 wt %.

H): A cosmetic agent for temporary deformation of keratinic fibers, particularly human hair, containing, in a cosmetic carrier, at least one starch modified with propylene oxide that has been degraded with hydrogen peroxide and has an average molecular weight (weight average) from 100 to 400 kDa, more preferably from 200 to 300 kDa, as well as a propylene oxide content, based on weight of the starch, from 8 to 12 wt %.

I): A cosmetic agent for temporary deformation of keratinic fibers, particularly human hair, containing, in a cosmetic carrier, at least one starch modified with propylene oxide that has been degraded with hydrogen peroxide and has an average molecular weight (weight average) from 100 to 400 kDa, more preferably from 200 to 300 kDa, as well as a propylene oxide content, based on weight of the starch, from 9.5 to 10.5 wt %.

J): A cosmetic agent for temporary deformation of keratinic fibers, particularly human hair, containing, in a cosmetic carrier, at least one uncrosslinked starch modified with propylene oxide and having an average molecular weight (weight average) from 50 to 2500 kDa, preferably from 700 to 900 kDa, the starch having a propylene oxide content, based on weight of the starch, from 5 to 15 wt %.

K): A cosmetic agent for temporary deformation of keratinic fibers, particularly human hair, containing, in a cosmetic carrier, at least one uncrosslinked starch modified with propylene oxide and having an average molecular weight (weight average) from 50 to 2500 kDa, preferably from 700 to 900 kDa, the starch having a propylene oxide content, based on weight of the starch, from 8.0 to 12.0 wt %.

L): A cosmetic agent for temporary deformation of keratinic fibers, particularly human hair, containing, in a cosmetic carrier, at least one uncrosslinked starch modified with propylene oxide and having an average molecular weight (weight average) from 50 to 2500 kDa, preferably from 700 to 900 kDa, the starch having a propylene oxide content, based on weight of the starch, from 9.5 to 10.5 wt %.

M): A cosmetic agent for temporary deformation of keratinic fibers, particularly human hair, containing, in a cosmetic carrier, at least one with uncrosslinked starch modified with propylene oxide and having an average molecular weight (weight average) from 100 to 1000 kDa, more preferably from 700 to 900 kDa, a viscosity from 10,000 to 100,000 mPa·s, preferably from 40,000 to 70,000 mPa·s, and a propylene oxide content, based on weight of the starch, from 5 to 15 wt %.

N): A cosmetic agent for temporary deformation of keratinic fibers, particularly human hair, containing, in a cosmetic carrier, at least one with uncrosslinked starch modified with propylene oxide and having an average molecular weight (weight average) from 100 to 1000 kDa, more preferably from 700 to 900 kDa, and a propylene oxide content, based on weight of the starch, from 8 to 12 wt %.

O): A cosmetic agent for temporary deformation of keratinic fibers, particularly human hair, containing, in a cosmetic carrier, at least one with uncrosslinked starch modified with propylene oxide and having an average molecular weight (weight average) from 100 to 1000 kDa, more preferably from 700 to 900 kDa, and a propylene oxide content, based on weight of the starch, from 9.5 to 10.5 wt %.

P): A cosmetic agent for temporary deformation of keratinic fibers, particularly human hair, containing, in a cosmetic carrier,
(a) at least one uncrosslinked starch modified with propylene oxide having an average molecular weight (weight average) from 100 to 1000 kDa, more preferably from 700 to 900 kDa, and having a propylene oxide content, based on weight of the starch, from 5 to 15 wt %, and
(b) at least one additional polymer, with the proviso that all additional polymers are polysaccharide-based polymers.

Q): A cosmetic agent for temporary deformation of keratinic fibers, particularly human hair, containing, in a cosmetic carrier,
(a) at least one uncrosslinked starch modified with propylene oxide having an average molecular weight (weight average) from 100 to 1000 kDa, more preferably from 700 to 900 kDa, and having a propylene oxide content, based on weight of the starch, from 8 to 12 wt %, and
(b) at least one additional polymer, with the proviso that all additional polymers are polysaccharide-based polymers.

R): A cosmetic agent for temporary deformation of keratinic fibers, particularly human hair, containing, in a cosmetic carrier,
(a) at least one uncrosslinked starch modified with propylene oxide having an average molecular weight (weight average) from 100 to 1000 kDa, more preferably from 700 to 900 kDa, and having a propylene oxide content, based on weight of the starch, from 9.5 to 10.5 wt %, and
(b) at least one additional polymer, with the proviso that all additional polymers are polysaccharide-based polymers.

S): A cosmetic agent for temporary deformation of keratinic fibers, particularly human hair, containing, in a cosmetic carrier, at least one with uncrosslinked potato starch modified with propylene oxide having an average molecular weight (weight average) from 100 to 1000 kDa, more preferably from 700 to 900 kDa, and a propylene oxide content, based on weight of the starch, from 5 to 15 wt %.

T): A cosmetic agent for temporary deformation of keratinic fibers, particularly human hair, containing, in a cosmetic carrier, at least one with uncrosslinked potato starch modified with propylene oxide having an average molecular weight (weight average) from 100 to 1000 kDa, more preferably from 700 to 900 kDa, and a propylene oxide content, based on weight of the starch, from 8 to 12 wt %.

U): A cosmetic agent for temporary deformation of keratinic fibers, particularly human hair, containing, in a cosmetic carrier, at least one with uncrosslinked potato starch modified with propylene oxide having an average molecular weight (weight average) from 100 to 1000 kDa, more preferably from 700 to 900 kDa, a viscosity from 10,000 to 100,000 mPa·s, preferably from 40,000 to 70,000 mPa·s, and a propylene oxide content, based on weight of the starch, from 5 to 15 wt %.

V): A cosmetic agent for temporary deformation of keratinic fibers, particularly human hair, containing, in a cosmetic carrier, at least one with uncrosslinked potato starch modified with propylene oxide having an average molecular weight (weight average) from 100 to 1000 kDa, more preferably from 700 to 900 kDa, a viscosity from 10,000 to 100,000 mPa·s, preferably from 40,000 to 70,000 mPa·s, and a propylene oxide content, based on weight of the starch, from 8 to 12 wt %.

W): A cosmetic agent for temporary deformation of keratinic fibers, particularly human hair, containing, in a cosmetic carrier, at least one with uncrosslinked potato starch modified with propylene oxide having an average molecular weight (weight average) from 100 to 1000 kDa, more preferably from 700 to 900 kDa, a viscosity from 10,000 to 100,000 mPa·s, preferably from 40,000 to 70,000 mPa·s, and a propylene oxide content, based on weight of the starch, from 9.5 to 10.5 wt %.

The viscosities of embodiments A to W, when listed, are defined according to the measurement conditions recited earlier.

The respective features of the agent characterized as preferred, such as the utilization quantities, of course apply mutatis mutandis in the embodiments recited above.

Further addition of at least one compound of formula (I)

$$HO-CH_2-(CHOH)_n-CH_2-OH \qquad (I),$$

wherein n is a whole number from 1 to 4, is preferably suitable for improving the effects according to the present invention.

Agents according to the present invention prove to be particularly effective when they contain glycerol and/or sorbitol as compounds of formula (I).

A utilization quantity of compounds of formula (I) in the range from 0.2 to 10 wt %, particularly from 0.5 to 7 wt %, has proven to be advantageous.

It is preferred to additionally use at least one nonionic surfactant. These surfactants can, according to the present invention, have an emulsifying effect.

Nonionic surfactants contain as a hydrophilic group, for example, a polyol group, a polyalkylene glycol ether group, or a combination of a polyol and polyglycol ether group. Such compounds include:

addition products of 2 to 100 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, addition products of 2 to 20 units of glycerol with linear or branched fatty alcohols having 8 to 30 carbon atoms in the alkyl group, with linear or branched fatty acids having 8 to 30 carbon atoms in the alkyl group such as the grades obtainable under the marketing designations Dermofeel® G 10 LW (Straetmans Chemical Products), addition products, end-capped with a methyl or $C_2$ to $C_6$ alkyl residue, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as the grades obtainable under the marketing designations Dehydrol® LS, Dehydrol® LT (Cognis), $C_{12}$ to $C_{30}$ fatty acid mono- and diesters of addition products of 1 to 30 mol ethylene oxide with glycerol, addition products of 5 to 60 mol ethylene oxide with castor oil and hardened castor oil, polyol fatty acid esters such as the commercial product Hydagen® HSP (Cognis), or Sovermol® grades (Cognis), alkoxylated triglycerides, alkoxylated fatty acid alkyl esters of formula (E4-I)

$$R^1CO-(OCH_2CHR^2)_w OR^3 \quad (E4\text{-}I),$$

wherein $R^1CO$ is a linear or branched, saturated and/or unsaturated acyl residue having 6 to 22 carbon atoms, $R^2$ is hydrogen or methyl, $R^3$ is linear or branched alkyl residues having 1 to 4 carbon atoms, and w is a number from 1 to 20, amine oxides, hydroxy mixed ethers such as those described in German Patent Application 19 73 8866, sorbitan fatty acid esters and addition products of ethylene oxide with sorbitan fatty acid esters, for example the polysorbates, sugar fatty acid esters and addition products of ethylene oxide with sugar fatty acid esters, addition products of ethylene oxide with fatty acid alkanolamides and fatty amines, sugar surfactants of the alkyl and alkenyl oligoglycoside types according to formula (E4-II)

$$R^4O-[G]_p \quad (E4\text{-}II),$$

wherein $R^4$ is an alkyl or alkenyl residue having 4 to 22 carbon atoms, G is a sugar residue having 5 or 6 carbon atoms, and p is a number from 1 to 10. They can be obtained in accordance with relevant methods of preparative organic chemistry.

Alkyl and alkenyl oligoglycosides can be derived from aldoses or ketoses having 5 or 6 carbon atoms, preferably from glucose. Preferred alkyl or alkenyl oligoglycosides are thus alkyl and/or alkenyl oligoglucosides. The index number p in the general formula (E4-II) indicates the degree of oligomerization (DP) (i.e., the distribution of mono- and oligoglycosides) and is a number from 1 to 10. Whereas p in the individual molecule must always be a whole number, and here can especially be the values p=1 to 6, the value p for a specific alkyl oligoglycoside is an analytically ascertained calculated value that usually represents a fractional number. Alkyl and/or alkenyl oligoglycosides having an average degree of oligomerization p from 1.1 to 3.0 are preferably used. In terms of applications engineering, those alkyl and/or alkenyl oligoglycosides whose degree of oligomerization is less than 1.7, and particularly from 1.2 to 1.4, are preferred. The alkyl or alkenyl residue $R^4$ can be derived from primary alcohols having 4 to 11, preferably 8 to 10 carbon atoms. Typical examples are butanol, hexanol, octanol, decanol, and undecyl alcohol, as well as industrial mixtures thereof, such as those obtained upon hydrogenation of industrial fatty acid methyl esters or in the course of the hydrogenation of aldehydes from Roelen oxosynthesis. Preferred are alkyl oligoglucosides of chain length $C_8$ to $C_{10}$ (DP=1 to 3), which occur as the first runnings upon distillational separation of industrial $C_8$ to $C_{18}$ coconut oil alcohol and can be contaminated with a proportion of less than 6 wt % $C_{12}$ alcohol, as well as alkyl oligoglucosides based on industrial $C_{9/11}$ oxoalcohols (DP=1 to 3). The alkyl or alkenyl residue $R^{15}$ can furthermore also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and industrial mixtures thereof, which can be obtained as described above. Alkyl oligoglucosides based on hardened $C_{12/14}$ coconut alcohol having a DP of 1 to 3 are preferred.

Particularly preferred for use in the agent according to the present invention are those nonionic surfactants chosen from addition products of 2 to 20 units of glycerol with linear or branched fatty alcohols having 8 to 30 carbon atoms in the alkyl group, addition products of 2 to 20 units of glycerol with linear or branched fatty acids having 8 to 30 carbon atoms in the alkyl group, addition products of 5 to 60 mol ethylene oxide with castor oil and hardened castor oil, sugar surfactants of the alkyl and alkyenyl oligoglycoside types, according to the above formula (E4-II), mixtures of the aforesaid surfactants.

Nonionic surfactants are present in the agent preferably in an amount from 0.005 wt % to 10 wt %, particularly 0.01 wt % to 2 wt %, based on weight of the agent.

The agents according to the present invention can also additionally contain at least one plant extract.

These extracts are usually produced by extraction of the entire plant. In individual cases, however, it may also be preferred to produce the extracts exclusively from blossoms and/or leaves of the plant.

Suitable plant extracts are obtained by extraction using organic solvents (e.g., ethanol, isopropanol, diethyl ether, naphtha, benzene, chloroform) or by steam distillation. Preferred extracts according to the present invention are from bamboo, linseed, white lotus, green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root.

The additional plant extract is present in the agent preferably in an amount from 0.05 wt % to 1.0 wt %, particularly 0.1 wt % to 0.5 wt %, based on weight of the cosmetic agent.

It is preferred, particularly if the agent is formulated as a cream, that the cosmetic agent according to the present invention additionally contains at least one oil phase.

An "oil phase" according to the present invention refers to a phase, liquid at 20° C., that dissolves at a proportion of less than 1 g in 100 g water at 20° C.

The oil phase preferably has a viscosity of up to 1000 mPa·s (Brookfield, RVDV II+, 20° C., 20 rpm, spindle 1).

In a preferred embodiment, the oil of the oil phase is chosen from at least one oil of—
  vegetable oils,
  animal oils,
  ester oils,
  liquid fatty acids and/or their mono-, di-, and trifatty acid esters of saturated and/or unsaturated linear and/or branched $C_6$ to $C_{22}$ fatty acids with glycerol.

Preferred vegetable oils are chosen from at least one of amaranth oil, sunflower oil, olive oil, soy oil, rapeseed oil, castor oil, sesame oil, almond oil, jojoba oil, orange oil, apricot kernel oil, macadamia nut oil, wheat germ oil, peach kernel oil, and the liquid components of coconut oil.

Preferred ester oils are chosen from esters of $C_6$ to $C_{30}$ fatty acids with $C_2$ to $C_{30}$ fatty alcohols. The monoesters of the fatty acids with alcohols having 2 to 24 carbon atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid, as well as industrial mixtures thereof that occur, for example, upon high-pressure cleavage of natural fats and oils, oxidation of aldehydes from Roelen oxosynthesis, or dimerization of unsaturated fatty acids. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Particularly preferred according to the present invention are isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

In particular, triglyceride esters of capric acid and caprylic acid (INCI name: Caprylic/Capric Triglyceride), obtainable, for example, as a commercial product of the Cognis company under the designation Myritol® 312, are preferred as mono-, di-, and trifatty acid esters of saturated and/or unsaturated linear and/or branched fatty acids with glycerol usable as an oil in the oil phase.

The additional oil phase is present in the agent preferably in an amount from 0.05 wt % to 25 wt %, particularly 0.1 wt % to 20 wt %, based on the weight of the cosmetic agent.

Agents according to the present invention that additionally contain at least one fatty substance are further suitable.

A "fatty substance" according to the present invention refers to those compounds that are soluble at a proportion of less than 1 g in 100 g water at 20° C.

The fatty substance is preferably chosen from at least one of candelilla wax, shea butter, carnauba wax, beeswax, coconut fat, $C_{12}$ to $C_{20}$ fatty acids (particularly palmitic acid, stearic acid).

The additional fatty substance is present in the agent preferably in an amount from 0.05 wt % to 35 wt %, particularly 1 wt % to 20 wt %, based on weight of the cosmetic agent.

The cosmetic agent according to the present invention can also contain additional adjuvants and additives, preferably using only those raw materials that do not originate in fossil fuels.

Care-providing substances can be recited in particular as suitable adjuvants and additives.

Agents according to the present invention contain their active substances in a cosmetic carrier, preferably in a water-containing cosmetic carrier, alcoholic cosmetic carrier, or an aqueous alcoholic cosmetic carrier. For temporary hair deformation, such carriers include lotions, water-in-oil emulsions, oil-in-water emulsions, creams, gels, foams, pomades, waxes, or other preparations that are suitable for use on the hair.

"Aqueous alcoholic" carriers for purposes of the present invention refer to aqueous compositions containing 3 to 70 wt % of a $C_1$ to $C_4$ alcohol, particularly ethanol or isopropanol. The agents can additionally contain further organic solvents such as methoxybutanol, benzyl alcohol, ethyl diglycol, 1,2-propylene glycol, or 1,3-propylene glycol. All water-soluble organic solvents are preferred in this context.

A cationic surfactant can be used as a care-providing substance. Cationic surfactants of the quaternary ammonium compound, esterquat, and amidoamine types are preferred. Preferred quaternary ammonium compounds are ammonium halides, particularly chlorides and bromides such as alkyltrimethylammonium chlorides, dialkyldimethylammonium chlorides, and trialkylmethylammonium chlorides (e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride), as well as the imidazolium compounds known by the INCI names Quaternium-27 and Quaternium-83. Long alkyl chains of the aforementioned surfactants preferably have 10 to 18 carbon atoms. Because the addition of surface-active substances can have a negative effect on the hydrophobic properties of hydrophobized silicon dioxide and thus on the stability of the cosmetic agent, the amount of care-providing surfactant must be carefully coordinated with the overall composition. The addition of surfactant constituents is preferably omitted.

Care-providing polymers are likewise suitable as a care-providing substance.

A first group of care-providing polymers is the cationic polymers. "Cationic polymers" refer to polymers having in the main chain and/or side chain a group that can be "temporarily" or "permanently" cationic. According to the present invention, those polymers having a cationic group regardless of the pH of the agent are referred to as "permanently cationic." These are polymers having a quaternary nitrogen atom, for example, in the form of an ammonium group. Preferred cationic groups are quaternary ammonium groups.

Also included among the cationic polymers are cationized protein hydrolysates, wherein the underlying protein hydrolysate can be derived from animals (e.g., from collagen, milk, or keratin), from plants (e.g., from wheat, corn, rice, potatoes, soy, or almonds), from marine life forms (e.g., from fish collagen or algae), or from biotechnologically obtained protein hydrolysates. The protein hydrolysates serving as the basis for the cationic derivatives according to the present invention can be obtained from the corresponding proteins by way of chemical, particularly alkaline or acid, hydrolysis, by enzymatic hydrolysis, and/or by combination of the two types of hydrolysis. Hydrolysis of proteins results in a protein hydrolysate having a molecular weight distribution from approximately 100 Dalton up to several thousand Dalton. Those cationic protein hydrolysates whose underlying protein component has a molecular weight from 100 to 25,000 Dalton, preferably 250 to 5,000 Dalton, are preferred. Cationic protein hydrolysates also include quaternized amino acids and mixtures thereof. Quaternization of the protein hydrolysates or of the amino acids is often carried out by quaternary ammonium salts such as N,N-dimethyl-N-(n-alkyl)-N-(2-hydroxy-3-chloro-n-propyl)ammonium halides. The cationic protein hydrolysates can also be further derivatized. Typical examples that may be mentioned of cationic protein hydrolysates and derivatives according to the present invention are the following products listed under the INCI names in the "International Cosmetic Ingredient Dictionary and Handbook," ($7^{th}$ Edition (1997), The Cosmetic, Toiletry, and Fragrance Association, 1101 $17^{th}$ Street, N.W., Suite 300, Washington, D.C. 20036-4702), and available commercially: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Plant-based cationic protein hydrolysates and derivatives are preferred.

Further care-providing polymers usable according to the present invention are amphoteric polymers.

It is further possible to use as a care-providing substance at least one vitamin, provitamin, vitamin precursor, and/or derivative thereof.

Those vitamins, provitamins, and vitamin precursors usually assigned to groups A, B, C, E, F, and H are preferred according to the present invention. Vitamins that belong the B group or to the vitamin B complex are particularly preferred, very particularly preferably vitamin $B_5$ (pantothenic acid, panthenol, and pantolactone).

A number of carboxylic acids are also suitable as a care-providing substance.

Short-chain carboxylic acids, in particular, can be advantageous for purposes of the invention. "Short-chain carboxylic acids" and derivatives thereof refer to carboxylic acids that can be saturated or unsaturated and/or straight-chain or branched or cyclic and/or aromatic and/or heterocylic, and have a molecular weight of less than 750. Saturated or unsaturated straight-chain or branched carboxylic acids having a chain length from 1 to 16 carbon atoms in the chain are preferred. Those having a chain length from 1 to 12 carbon atoms in the chain are very particularly preferred.

Further suitable care-providing substances are protein hydrolysates and/or derivatives thereof. Use of protein hydrolysates of vegetable origin (e.g., soy, almond, bean, potato, and wheat protein hydrolysates) is preferred. Such products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda).

Although use of protein hydrolysates as such is preferred, it is also optionally possible to instead use, if applicable, amino-acid mixtures obtained in different fashion. It is likewise possible to use derivatives of protein hydrolysates, for example in the form of their fatty acid condensation products. Such products are marketed, for example, under the designations Lamepon® (Cognis), Lexein® (Index), Crolastin® (Croda), Crosilk® (Croda), or Crotein® (Croda).

The teaching of the present invention includes all isomeric forms, such as cis-trans isomers, diastereomers, and chiral isomers.

It is also possible according to the present invention to use a mixture of multiple protein hydrolysates.

Also suitable as a care-providing substance are lipids and oily substances, for example, vegetable oils, liquid paraffin oils, isoparaffin oils, synthetic hydrocarbons and ester oils, enzymes, and pearl extracts.

In addition to the care-providing substances, further adjuvants and additives can also be added.

The addition of a UV filter allows both the preparations and the treated fibers to be protected from damaging influences of UV radiation. It can therefore be advantageous to add at least one UV filter to cosmetic agents according to the present invention. Suitable UV filters are not subject to any general restrictions in terms of their structure and their physical properties. Instead, all UV filters usable in the cosmetics sector whose absorption maximum lies in the UVA (315 to 400 nm) UVB (280 to 315 nm), or UVC (<280 nm) regions, are suitable. UV filters having an absorption maximum in the UVB region, particularly from approximately 280 to approximately 300 nm, are particularly preferred.

Preferred UV filters include substituted benzophenones, p-aminobenzoic acid esters, diphenylacrylic acid esters, cinnamic acid esters, salicylic acid esters, benzimidazoles, and o-aminobenzoic acid esters. Examples that may be recited here are 2-hydroxy-4-methoxybenzophenone-5-sulfonic acid and the sodium salt thereof (Benzophenone-4; Uvinul® MS 40; Uvasorb® S 5).

In a particular embodiment, the cosmetic agent further contains one or more substantive dyes. This allows the keratinic fibers treated with the agent to be not only temporarily structured, but at the same time also dyed. This can be particularly desirable when only a temporary color is desired, for example, with conspicuous "fashion" colors which can be removed from the keratinic fibers simply by washing.

Cosmetic agents according to the present invention can also contain alkalizing agents, usually alkali hydroxides or alkaline-earth hydroxides, ammonia, or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol, and triethanolamine, as well as alkali metal and alkaline-earth metal hydroxides. Monoethanolamine, triethanolamine, and 2-amino-2-methylpropanol and 2-amino-2-methyl-1,3-propanediol are particularly preferred. Use of co-amino acids such as co-aminohexanoic acid as an alkalizing agent is also possible.

A second subject of the invention is the use of a cosmetic agent of the first subject of the invention for temporary deformation and/or shape fixing of keratinic fibers, particularly human hair.

A third subject of the invention is a method for temporary deformation of keratinic fibers, particularly human hair, wherein a cosmetic agent of the first subject of the invention is applied onto the keratinic fibers.

It is preferred if the keratinic fibers, after application of the cosmetic agents of the first subject of the invention, are not rinsed and are left on the fibers.

The Examples that follow are intended to explain the subject matter of the present invention without in any way limiting them.

EXAMPLES

The following commercial products were used:
Plantacare® 818 UP C8-14 alkylpolyglucoside (approx. 51 to 53% active substance content; INCI name: Coco-Glucoside, Aqua (Water)) (Cognis)
Euxyl®PE 9010 Mixture of 90 wt % 2-phenoxyethanol and 10 wt % 3-(2-ethylhexyloxy)-1,2-propanediol (100 wt % active substance, INCI name: Phenoxyethanol, Ethylhexyl Glycerin) (Schülke & Mayr)

1.0 Styling Paste for Modeling—

TABLE 1

| RMG | Raw materials | Wt % |
|---|---|---|
| 1 | Water | 56.60 |
| 1 | Sodium hydroxide | 0.50 |
| 1 | Burdock root extract | 0.10 |
| 1 | Sorbitol | 2.10 |
| 1 | Plantacare ® 818 UP | 5.00 |
| 2 | Xanthan gum | 0.15 |
| 2 | Dehydroxanthan | 1.20 |
| 2 | Propylene oxide-modified tapioca starch * | 0.30 |
| 2 | Stearic acid | 4.00 |

TABLE 1-continued

| RMG | Raw materials | Wt % |
|---|---|---|
| 2 | Caprylic/Caprinic Acid Triglyceride | 3.00 |
| 2 | Locust bean flour | 0.10 |
| 2 | Guar gum | 0.05 |
| 2 | Palmitic acid | 2.00 |
| 2 | Candelilla wax | 3.50 |
| 2 | Isopropyl myristate | 7.00 |
| 2 | Shea butter | 1.00 |
| 2 | Carnauba wax | 7.00 |
| 2 | Beeswax | 5.00 |
| 3 | Euxyl PE 9010 ® | 1.00 |
| 3 | Lactic acid | 0.08 |
| 3 | Perfume | 0.50 |

* Tapioca starch modified with 10 wt % propylene oxide, molar mass 200 to 300 kDa.

Manufacture Process

Step I—The raw materials of Table 1 labeled as RMG 1 were made ready in a vessel. The mixture was heated to 75° C. while stirring.

Step II—The raw materials of Table 1 labeled as RMG 2 were made ready in a second vessel. The mixture was heated to 75° C. with gentle stirring.

Step III—When the temperatures of the two mixtures had stabilized at 75° C., the contents of the first vessel were transferred into the second vessel with vigorous stirring. After addition was completed, vigorous stirring was continued for at least 15 minutes.

Step IV—The raw materials of Table 1 labeled as RMG 3 were put into the second vessel and the resulting mixture was stirred for at least 10 minutes until homogeneous.

The resulting styling paste was highly suitable for separating individual hair portions. A matting effect was achieved. The hairstyle produced after using the styling paste had a strong hold and could be remodeled.

2.0 Styling Paste for Subduing Flyaway Hair—

TABLE 2

| RMG | Raw materials | Wt % |
|---|---|---|
| 1 | Water | 59.5 |
| 1 | Glycerol (vegetable) | 5.16 |
| 1 | Plantacare ® 818 UP | 4.50 |
| 2 | Shea butter | 1.50 |
| 2 | Stearic acid | 4.00 |
| 2 | Palmitic acid | 4.00 |
| 2 | Sesame oil | 0.10 |
| 2 | Linseed extract (in sunflower oil) | 0.20 |
| 2 | Candelilla wax | 2.00 |
| 2 | Isopropyl myristate | 10.00 |
| 2 | Caprylic/Caprinic Acid Triglyceride | 7.00 |
| 3 | Propylene oxide-modified tapioca starch ** | 0.50 |
| 3 | Dehydroxanthan | 0.50 |
| 4 | Euxyl PE 9010 ® | 1.00 |
| 4 | Lactic acid | 0.04 |
| 4 | Perfume | 0.50 |

** Tapioca starch modified with 10 wt % propylene oxide, molar mass 700 to 900 kDa.

Manufacture Process

Step I—In a first vessel, the raw materials of Table 2 labeled as RMG 2 were heated to 85° C. while stirring until the phase had become homogeneous.

Step II—A second vessel was filled with the raw materials of Table 2 labeled as RMG 1, and the mixture was heated to 60° C. while stirring. Stirring was continued until the mixture was homogeneous and all the lumps had dissolved.

Step III—The raw materials of Table 2 labeled as RMG 3 were added to the mixture of the second vessel and incorporated with vigorous stirring. The mixture was then heated to 85° C. and stirred for at least 20 minutes until homogeneous.

Step IV—Once the temperatures of the two mixtures had stabilized at 85° C., the mixture of the second vessel was added to the mixture of the first vessel. The temperature was then stabilized at 80° C. and stirring occurred for a period of 100 minutes.

Step V—The mixture was then cooled to 40° C. while stirring, and the raw materials of Table 2 labeled as RMG 4 were then added. Lastly, the mixture was left to stir for at least 15 minutes until homogeneous and the mixture was then allowed to cool to ambient temperature.

The resulting styling paste subdues stubborn hair. The resulting hairstyle had good hold and a natural shine.

3.0 Demonstration of Effectiveness—

The following propylene oxide-modified starches were used:

TABLE 3

Propylene oxide-modified starches -

| Designation of modified starch | Average molecular weight of modified starch (kDa) | Viscosity of modified starch (mPa · s) |
|---|---|---|
| HPS A [1] | 700 to 900 | 64,000 |
| HPS B [2] | 1400 to 1800 | 170,000 |
| HPS C [3] | 200 to 300 | 6300 |
| HPS D [4] | 700 to 900 | 55,000 |

[1] Tapioca starch modified with 10 wt % propylene oxide
[2] Tapioca starch modified with 10 wt % propylene oxide and crosslinked
[3] Tapioca starch modified with 10 wt % propylene oxide and degraded with hydrogen peroxide
[4] Potato starch modified with 10 wt % propylene oxide All modified starch derivatives were capable of being dissolved or stably dispersed in water at a proportion of 5 wt % or 10 wt %.

5-wt % polymer solutions of each of the respective hydroxypropyl starches HPS A to D, and of polyvinylpyrrolidone/vinyl acetate copolymer (PVP/VA) (Luviskol® 64 W NP, BASF SE) in water were produced. Omega loop measurements and measurements of curl retention were then carried out on hair strands treated therewith. Hair strands were investigated for this purpose using the procedure described in sections 4.0 and 5.0.

The following results were obtained:

a) Hold, Elasticity, and Flexibility (Omega Loop Method)

TABLE 4

Hold, elasticity, flexibility -

| Polymer solution | F max (N) | Elasticity | Flexibility |
|---|---|---|---|
| HPS A—5 wt % | 1.3 | 65% | 68% |
| HPS B—5 wt % | 1.1 | 34% | 67% |
| HPS C—5 wt % | 1.3 | 53% | 74% |
| HPS D—5 wt % | 1.2 | 50% | 70% |
| PVP/VA—5 wt % | 1.1 | 34% | 67% |

The higher the F max values, the better the hairstyle hold. The values in Table 2 confirm that propylene oxide-modified starch derivatives according to the present invention yield a hairstyle hold that is comparable to—and in fact, when the propylene oxide-modified starch derivative has a low molecular weight, is even better than—the common film former PVP/VA.

The higher the values for elasticity or flexibility, the better the elasticity or flexibility of the hairstyle. Hair strands treated with agents according to the present invention exhibited a more flexible and more elastic hold than strands that had been treated with PVP/VA copolymer.

These trends remained evident when higher polymer concentrations (10 wt %) were used.

b) High Humidity Curl Retention (HHCR)

TABLE 3

High humidity curl retention (HHCR) -

| Polymer solution | HHCR |
|---|---|
| HPS A—5 wt % | 45% |
| HPS B—5 wt % | 59% |
| HPS C—5 wt % | 52% |
| HPS D—5 wt % | 75% |
| PVP/VA—5 wt % | 44% |

Hair strands treated with the agent according to the present invention exhibited a hairstyle hold that was more resistant to humidity.

This trend remained evident when higher polymer concentrations (10 wt %) were used.

4.0 Performing the Omega Loop Measurement—

Deformation hold, also called "hairstyle hold," as well as flexibility and elasticity, was determined for purposes of the present invention using the omega loop method.

For this, a dry hair strand (European Natural hair of the Kerling company, bonded dense tress, bonded at one end, total length 160 mm, free length 150 mm, width 10 mm, weight 1.0±0.1 g) is immersed for 30 seconds into the polymer solution to be investigated as far as the lower edge of the adhesive bond. The excess solution is then wiped off between the thumb and forefinger so that 0.5±0.02 g of solution remains on the hair. The hair strand, saturated with the solution to be investigated, is wound around a Teflon cylinder 36 mm in diameter, and the projecting ends are secured with a clip. The prepared strands are then dried and conditioned in an environmental chamber overnight at 25° C. and 50% relative humidity, or at 25° C. and 75% relative humidity.

The conditioned strand is carefully removed from the Teflon cylinder. The resulting omega loop—a ring-shaped structure of hair stabilized in shape by the polymer film that has formed—is clamped into the grippers mounted on the load cell and lowered to just above the baseplate of an AMETEK LF Plus universal testing instrument of AMETEK Precision Instruments Europe GmbH, Lloyd product group. The entire measurement is performed in an environmental chamber under constant climatic conditions, at 25° C. and 50% relative humidity or at 25° C. and 75% relative humidity.

In order to create standardized initial conditions, the measurement begins with application of a preload of 0.07 N at a rate of 30 mm min$^{-1}$. The omega loop is then compressed 8 mm at a rate of 60 mm min$^{-1}$, the force required being measured. Once the characteristic force $F_1$ at the maximum deformation of 8 mm has been recorded, the strand is unloaded at 60 mm min$^{-1}$ until it has risen 10 mm from the baseplate. The next cycle begins from there by once again applying the 0.07 N preload and then compressing the strand 8 mm; applicable rates are the same as described above. Measurement of one omega loop comprises a total of 10 cycles.

Four characteristic parameters for describing the mechanical properties of film-forming polymers can be determined using this measurement method. Hold, flexibility, plasticity, and elasticity can be calculated from the measured forces using the following formulae:

$$\text{Hold} = F_1 [N]$$

($F_1$ corresponds to maximum measurement force)

$$\text{Flexibility} = \frac{F_{10}}{F_1}$$

(indicates the ratio of maximum forces between the tenth ($F_{10}$) and the first cycle ($F_1$))

$$\text{Elasticity} = \frac{\frac{F_{10}(2\text{ mm}) - F_{10}(1,5\text{ mm})}{0,5}}{\frac{F_1(2\text{ mm}) - F_1(1,5\text{ mm})}{0,5}} = \frac{E_{10}}{E_1}$$

(to calculate elasticity, the forces for a 1.5 mm and 2 mm deformation are acquired respectively from the first and the tenth cycle and are correlated).

5.0 Performing the High Humidity Curl Retention Measurement—

Standardized hair strands of the Kerling company (item no. 827560), hair type "European Natural," color 6/0, with a length ($L_{max}$) of 220 mm and a weight of 0.6 g, were used. For preparation, the strands were washed with 12.5-wt % sodium laureth sulfate solution. The hair strands were dried overnight in a drying oven at 318° K.

0.18 g of the compositions was applied onto each hair strand and massaged in. The strands were then wound onto a curler (Fripac-medis, diam. 7 mm, item no. D-1203) and dried overnight at room temperature.

The curlers were then carefully removed, and the strands suspended. The length of each of the curls was measured ($L_0$), and the strands were put into a climate chamber. They were stored there at 294° K and a relative humidity of 85% for a period of 24 hours, and the lengths of the curls were then measured again ($L_t$).

Five test strands were correspondingly treated and measured for each composition.

High humidity curl retention (HHCR) was calculated using the formula below, and the arithmetic mean of HHCR values for the five test strands was obtained for each composition:

$$HHCR = \frac{L_{max} - L_t}{L_{max} - L_0}$$

We claim:

1. Cosmetic agent for temporary deformation of keratinic fibers comprising, in a cosmetic carrier:
at least one starch modified with propylene oxide having an average molecular weight (weight average) from 100 to 1000 kDa.

2. Cosmetic agent according to claim 1, wherein the modified starch has an average molecular weight (weight average) from 700 to 900 kDa.

3. Cosmetic agent according to claim 1, wherein the modified starch has a propylene oxide content from 5 to 15 wt %, based on weight of the starch.

4. Cosmetic agent according to claim 3, wherein the modified starch has a propylene oxide content from 8 to 12 wt %, based on weight of the starch.

5. Cosmetic agent according to claim 1, wherein the modified starch has, in a 43-wt % aqueous solution, a viscosity in a range from 150 to 1,500,000 mPa·s (Brookfield viscosimeter, spindle 7 at 20° C. and 20 rpm).

6. Cosmetic agent according to claim 5, wherein the modified starch has, in a 43-wt % aqueous solution, a viscosity in the range from 10,000 to 100,000 mPa·s (Brookfield viscosimeter, spindle 7 at 20° C. and 20 rpm).

7. Cosmetic agent according to claim 1, wherein the modified starch is a tapioca starch modified with propylene oxide, a potato starch modified with propylene oxide, or a mixture of tapioca and potato starches.

8. Cosmetic agent according to claim 1, wherein the modified starch is present in an amount from 1.0 wt % to 30 wt %, based on total weight of the agent.

9. Cosmetic agent according to claim 8, wherein the modified starch is present in an amount from 2.5 wt % to 20 wt %, based on total weight of the agent.

10. Cosmetic agent according to claim 1, wherein the modified starch is uncrosslinked.

11. Cosmetic agent for temporary deformation of keratinic fibers comprising, in a cosmetic carrier:
at least one starch modified with propylene oxide having an average molecular weight (weight average) from 50 to 2500 kDa and at least one additional polymer, with the proviso that all additional polymers are polysaccharide-based polymers.

12. Cosmetic agent according to claim 11, wherein the polysaccharide-based polymers are chosen from xanthan, dehydroxanthan, alginate, guar gum, gum arabic, locust bean gum, starch, chitosan, or mixtures.

13. Cosmetic agent according to claim 1, wherein the agent is in the form of a foam or gel.

14. Cosmetic agent according to claim 1 further comprising at least one compound of formula (I)

HO—$CH_2$—$(CHOH)_n$—$CH_2$—OH     (I), wherein n is a whole number from 1 to 4.

15. Method for the temporary deformation of keratinic fibers comprising applying a cosmetic agent according to claim 1 onto the keratinic fibers.

* * * * *